United States Patent [19]

Hungerford et al.

[11] Patent Number: 5,567,120

[45] Date of Patent: Oct. 22, 1996

[54] ELECTRONIC INFUSION DEVICE AND NOVEL ROLLER CLAMP HOLDEN THEREFOR

[75] Inventors: Roger L. Hungerford, Medina; Christopher D. Cimerman, Cheektowaga; Paul J. Hufnagel, Clarence; Robert J. Pieroni, Lewiston, all of N.Y.

[73] Assignee: Sigma International, Medina, N.Y.

[21] Appl. No.: 322,432

[22] Filed: Oct. 13, 1994

[51] Int. Cl.$^6$ .......................... F04B 49/00; F04B 43/09
[52] U.S. Cl. .............................. 417/63; 417/474; 604/250
[58] Field of Search .......................... 417/474, 63, 360; 604/34, 153, 250

[56] References Cited

U.S. PATENT DOCUMENTS

| | | | |
|---|---|---|---|
| 4,155,362 | 5/1979 | Jess | 128/214 F |
| 4,460,358 | 7/1984 | Somerville et al. | 604/250 |
| 4,586,691 | 5/1986 | Kozlow | 251/7 |
| 4,689,043 | 8/1987 | Bisha | 604/250 |
| 4,818,190 | 4/1989 | Pelmulder | 417/360 |
| 4,857,050 | 8/1989 | Lentz et al. | 604/67 |
| 4,878,896 | 11/1989 | Garrison et al. | 604/65 |
| 5,017,192 | 5/1991 | Dodge et al. | 604/250 |
| 5,039,279 | 8/1991 | Natwick et al. | 417/474 |
| 5,116,203 | 5/1992 | Natwick et al. | 417/474 |
| 5,219,327 | 6/1993 | Okada | 604/250 |
| 5,300,044 | 4/1994 | Classey et al. | 604/250 |
| 5,437,625 | 8/1995 | Fields et al. | 604/250 |
| 5,437,642 | 8/1995 | Thill et al. | 604/250 |
| 5,482,446 | 1/1996 | Williamson et al. | 417/474 |

*Primary Examiner*—Timothy S. Thorpe
*Assistant Examiner*—Peter G. Korytnyk
*Attorney, Agent, or Firm*—Shlesinger Fitzsimmons Shlesinger

[57] ABSTRACT

A holder for an IV tube roller clamp is removably secured in the housing of an electronic infusion device, and has in opposite ends thereof a pair of photo-electric devices, one of which detects when the roller of the clamp is in its tube opening position, and the other detects when the roller is in tube closing position. A lever is pivotal on the housing between a closed position in which it operatively connects the IV tube to a pump unit in the housing, and an open position in which it permits removal of the IV tube from the unit. The spring-loaded armature of a solenoid prevents the lever from being opened until the solenoid coil is energized, and the photo-electric devices prevent the solenoid coil from being energized until the roller is in its tube closing position. When closed, the lever overlies part of the tube channel in which the IV tube is seated and also shifts a pressure plate in the pump unit to a position in which a lip thereon overlies another portion of said channel.

20 Claims, 4 Drawing Sheets

ELECTRONIC INFUSION DEVICE AND NOVEL ROLLER CLAMP HOLDEN THEREFOR

BACKGROUND OF THE INVENTION

This invention relates to an improved electronic infusion device which causes the roller clamp of an intravenous administration set to interact with the device in such a way that dangerous, accidents gravity free flow will not occur. More specifically, the invention requires loading of the roller clamp into the infusion device and prevents removal of the IV set from the infusion device until the roller clamp is closed. This prevents fluid flow when the IV set is removed from the infusion device. It also enables a standard gravity IV set to become a "protected" set without the addition of any special components to the set.

By way of Definition

ELECTRONIC INFUSION DEVICES (EID), which are also known as infusion pumps or infusion controllers, are used accurately to regulate the flow rate of intravenous fluids and to electronically monitor and alarm should a variety of unsafe occurrences be detected relating to the infusion.

INTRAVENOUS (IV) SETS, also called IV sets or gravity sets, are single use, disposable, sterile, tubing sets that connect the IV fluid container (a bag or bottle) with the patients's catheter. IV sets are used either with EID's or n their own when the relatively inaccurate flow rates they are capable of providing are clinically acceptable.

ROLLER CLAMPS are components found on IV sets. They consist of an operator adjusted roller wheel mounted in a small plastic housing. The roller wheel pinches the IV tubing to varying degrees ranging from fully closed to partially open (which results in controlled gravity flow), to fully open When an IV set is loaded n an EID the roller is left fully open to allow the EID to control flow rate.

FREE FLOW occurs whenever an IV set is not in an EID and its roller clamp (and all other IV set clamps) are fully open. While there are a few clinical conditions where free flow is desirable, in most cases free flow refers to an accidental and dangerous condition that can lead to patient injury or death. These accidental free flow conditions most commonly occur when IV sets are removed from EID's without the operator remembering to close the sets roller clamp first.

PROTECTED IV SETS, as defined by ECR1 are either; dedicated infusion pump sets that include a special IV set component which interacts with the EID when the set is unloaded to prevent gravity free flow, or they are standard gravity IV sets whose roller clamps must be closed before the EID allows set removal.

[1]ECRI, Emergency Care Research Institute, is a non-profit organization that evaluates and reports on medical instrumentation to the health care industry.

Some prior art EIDs (such as the trademark VAC 500 and which used standard gravity IV sets employed doors to keep the tubing closed, preventing free flow while the tubing was held in the device. However, if the device's door was opened before the sets' roller clamp was closed, free-flow occurred. Other prior art EIDs (such as the SIGMA 5000) were equipped with both a door and a "flow stop". If the door was opened with an open roller clamp the spring activated flow stop would close the IV tubing to prevent free flow. This two step process to initiate gravity flow was considered the industry standard for preventing Free flow and still is the AAMI (American Association of Medical Instrumentation) standard.

However, due to the rising importance of preventing accidental free flow, ECRI (Emergency Care Research Insitute) has created a "quasi" standard. It states that in order to assure free-flow protection, either anti-free flow infusion sets ("protected sets") should be used with EIDs (an example being med's trademark Gemini V pump referenced in U.S. Pat. 2,689,043) or the EID design should force the operator to close the IV set's roller clamp prior to removing the set from the device.

The primary object of this invention is to provide an EID design that interacts with the roller clamp of a standard IV set in such a way that the clamp is always closed prior to removal of the set from the EID, thus preventing accidental free flow.

Still another objective is to be able to remove the EID's modular roller clamp holder so that it can be replaced with new roller clamp holders able to accommodate roller clamps of varying dimension. In this manner, the EID is compatible with the IV sets and roller clamps of multiple manufacturers.

Other objectives of this invention will be apparent hereinafter from the specification and from recital of the appended claims, particularly when read with the accompanying drawings.

SUMMARY

The invention includes a roller clamp holder mounted to open on the front face of the EID. Into this holder is loaded the IV set's roller clamp. The roller clamp holder includes an electronic power supply switch which causes the EID to turn on as soon as the roller clamp is loaded. The roller clamp holder also includes electronic detectors which are able to determine the roller wheel position, whether fully closed, partially open, or fully open. The roller clamp holder will accept most standard IV set roller clamps, and its modular removable design allows one holder to be replaced by another one to accommodate roller clamps of varying dimension.

Immediately below the roller clamp holder is the EID's peristaltic (tube squeezing) pumping mechanism. Extending through this mechanism is the pump section of a vertical tube channel into which the IV set tubing is loaded. On one side of the pump section of the channel are the peristaltic pump's fingers, which are push rods driven by the pump's camshaft. On the other side of this section is a pressure plate which is retracted to enable the loading of the IV set tubing. After the IV set tubing has been loaded into the tube channel, the pressure plate is advanced so that the registering tubing is squeezed between the pump fingers and the pressure plate. Once loaded, the tubing in the pump section is covered by an overlapping lip on the pressure plate which overlies the pump section of the tube channel. Thus loaded, the tubing cannot be unloaded until the pressure plate lip is pulled back out of the way, which in turn opens the tube channel. A lever located just below the peristaltic pump, is connected to the pressure plate. By means of this manually operated lever, the pressure plate is moved out of the way to facilitate IV tube loading and unloading.

The lever is controlled by a solenoid actuated locking mechanism. This mechanism is in turn controlled by the EID's electronics, specifically its micro controller. The lever remains locked at all times except when two consecutive events take place. These events are roller clamp holder detecting the roller wheel is closed and the load/unload key of the EID's key board being pushed. The combination of these two things causes the lever locking solenoid to actuate, which then results in the lever unlocking. The lever can then be opened and the pressure plate is pulled back so that its lip no longer overlaps the tubing. The tube channel is then open and the IV set can be removed safely with its closed roller clamp. When the lever is re-closed it remains locked until the next time both a closed roller is sensed and the load/unload key is pushed. When the IV set is locked in the peristaltic finger pumps one of the pump fingers is always in a fully outward position. This causes the IV tubing to be closed which prevents any flow when the pump is stopped and not running. As a consequence, the invention prevents both loading and unloading the IV set with the IV set's roller clamp in other than a fully closed, no flow position.

DRAWINGS

FIG. 1 is a front elevational view of an improved electronic infusion device having mounted therein a, modular roller clamp holder of the type made according to one embodiment of this invention, part of the front wall of the device being cut away for purposes of illustration, FIG. 2 is an enlarged fragmentary sectional view taken generally along the line 2—2 in FIG. 1 looking in the direction of the arrows, but with portions of the illustrated roller clamp being shown in full;

DETAILED DESCRIPTION OF THE PREFERRED EMBODIMENTS

Figure 1:
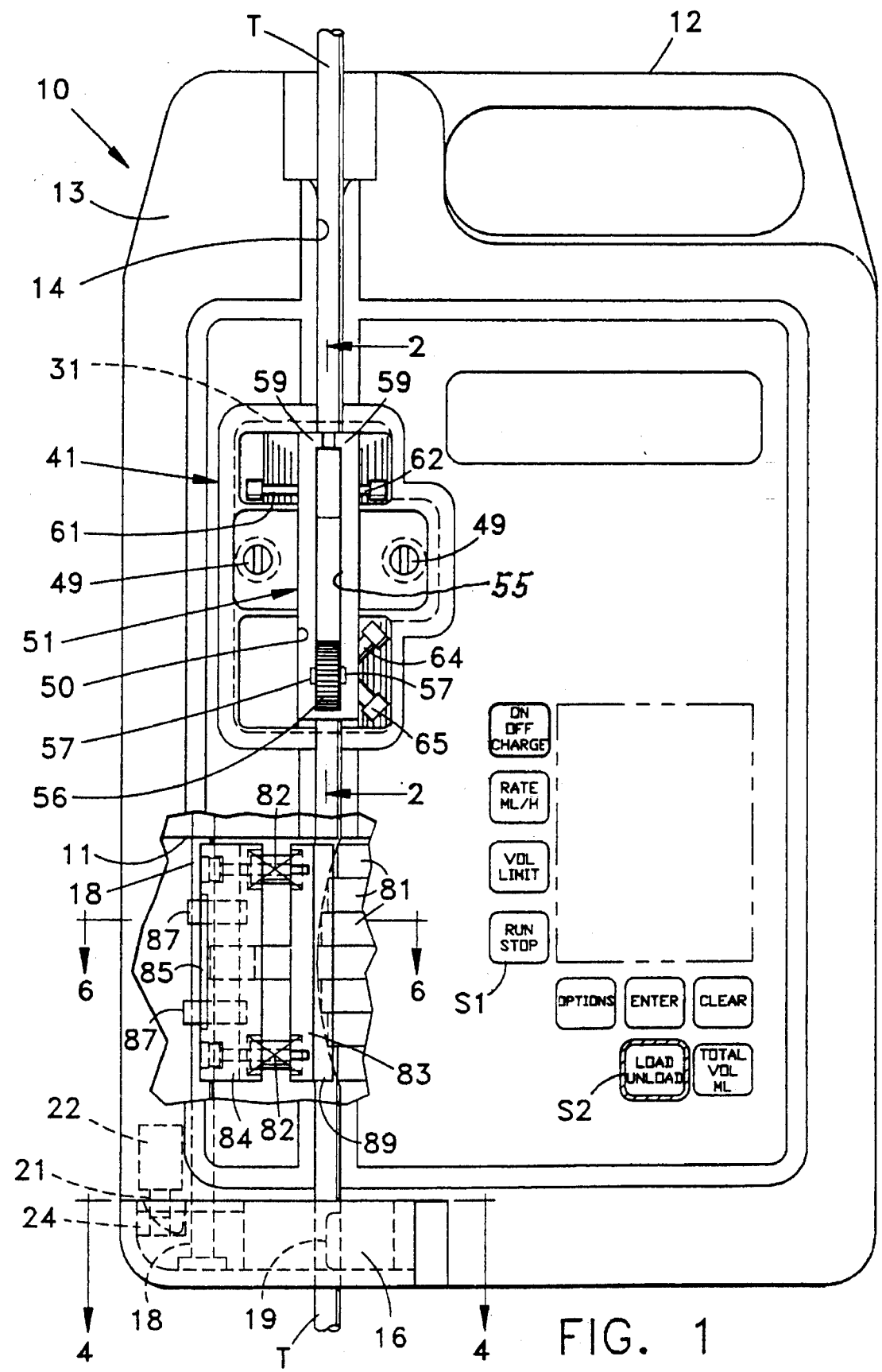

Referring now to the drawings by numerals of reference, and first to FIGS. 1 to 3, 10 denotes generally the housing of an electronic infusion device containing a linear peristaltic pump unit part of the upper wall 11 of which is illustrated in FIG. 1, and having a hand grip section or portion 12 for use in carrying the housing 10. The front wall 13 of housing 10 has therein an elongate, vertically extending I.V. tubing channel 14, which extends continuously between the upper and lower ends, respectively, of housing 10 for accommodating the tube T of a conventional IV. tubing set. Fluid flows from a supply thereof (not illustrated) through the tube T, and for example downwardly in FIG. 1, when the tube is mounted in housing 10 as described in greater detail hereinafter.

When the tube T is properly mounted in the housing 10, the tubing channel 14 in the front wall 13 is partially closed or covered by a lever 16, which is secured adjacent one end thereof (the left end in FIGS. 1 and 4) to a shaft 18 adjacent the lower end thereof. Shaft 18 is rotatably mounted at its lower end in the bottom of housing 10, and at its upper end in the pump wall 11 with its axis extending vertically and parallel to the axis of the tube- accommodating channel 14. Lever 16 is pivotal manually about shaft 18 between the closed position s shown by solid lines in FIGS. 1 and 4, and an open position as illustrated by broken lines in FIG. 4. When the lever 16 is in its closed position a projection 19 on the inside surface thereof registers with the tube T, which is seated in the tube channel 14. Also when lever 16 is moved to its closed position, the spring-loaded armature 21 of a solenoid 22, which is mounted in housing 10 above the lever 16, slides up a camming surface 23 on the lever and drops into a registering, annular boss 24 that is formed on the lever 16 adjacent shaft 18. In this manner lever 16 is locked or secured in its closed position until such time that the coil of solenoid 22 is energized in order to withdraw its armature 21 upwardly and out of the boss 24 in lever 16. Also when lever 16 is closed, a portion of the lever 16 overlies a portion of tube channel 14 and the tube T, thereby preventing, together with additional means noted hereinafter, removal of the tube from housing 10.

Figure 2:
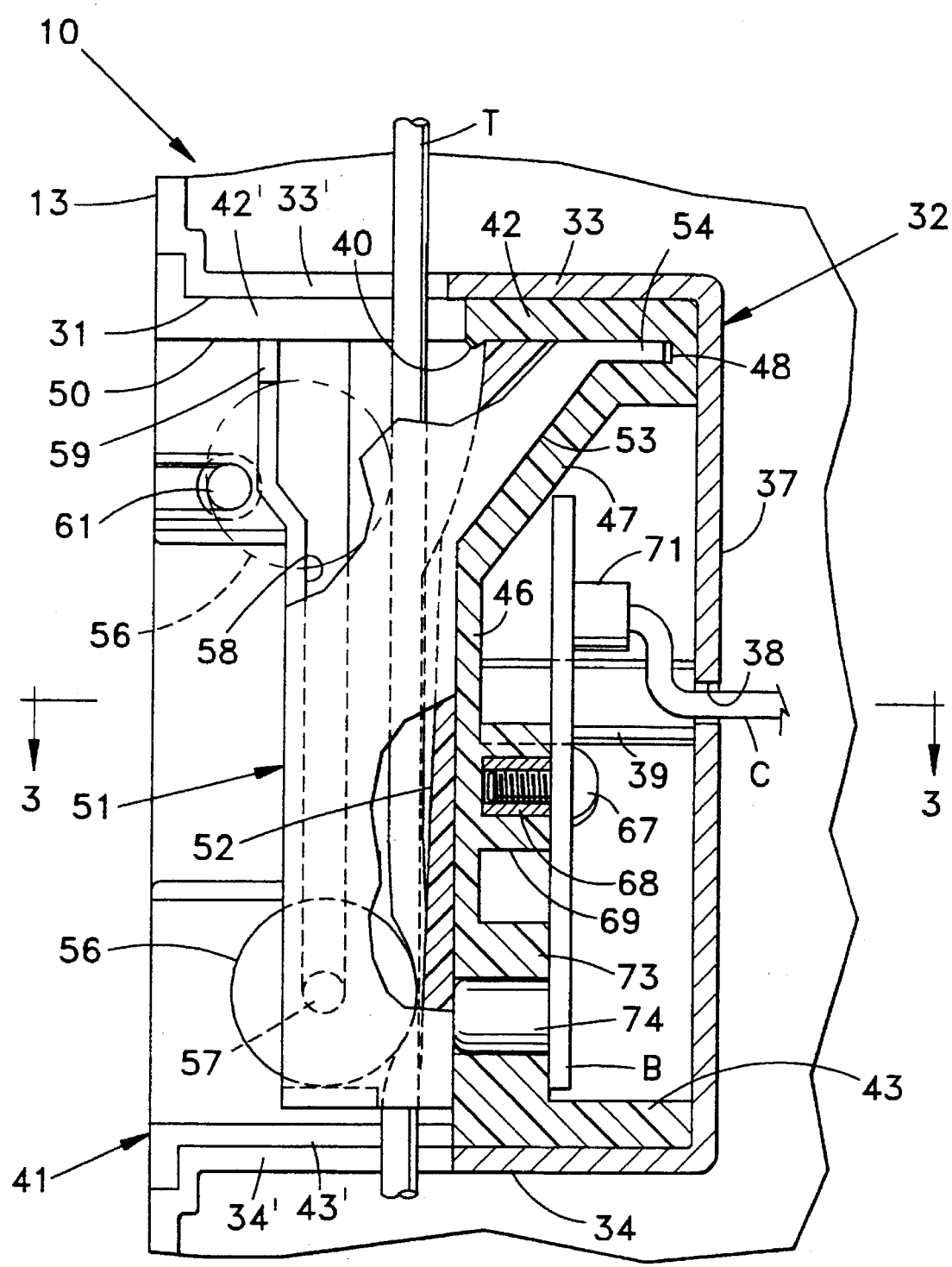
Figure 3:
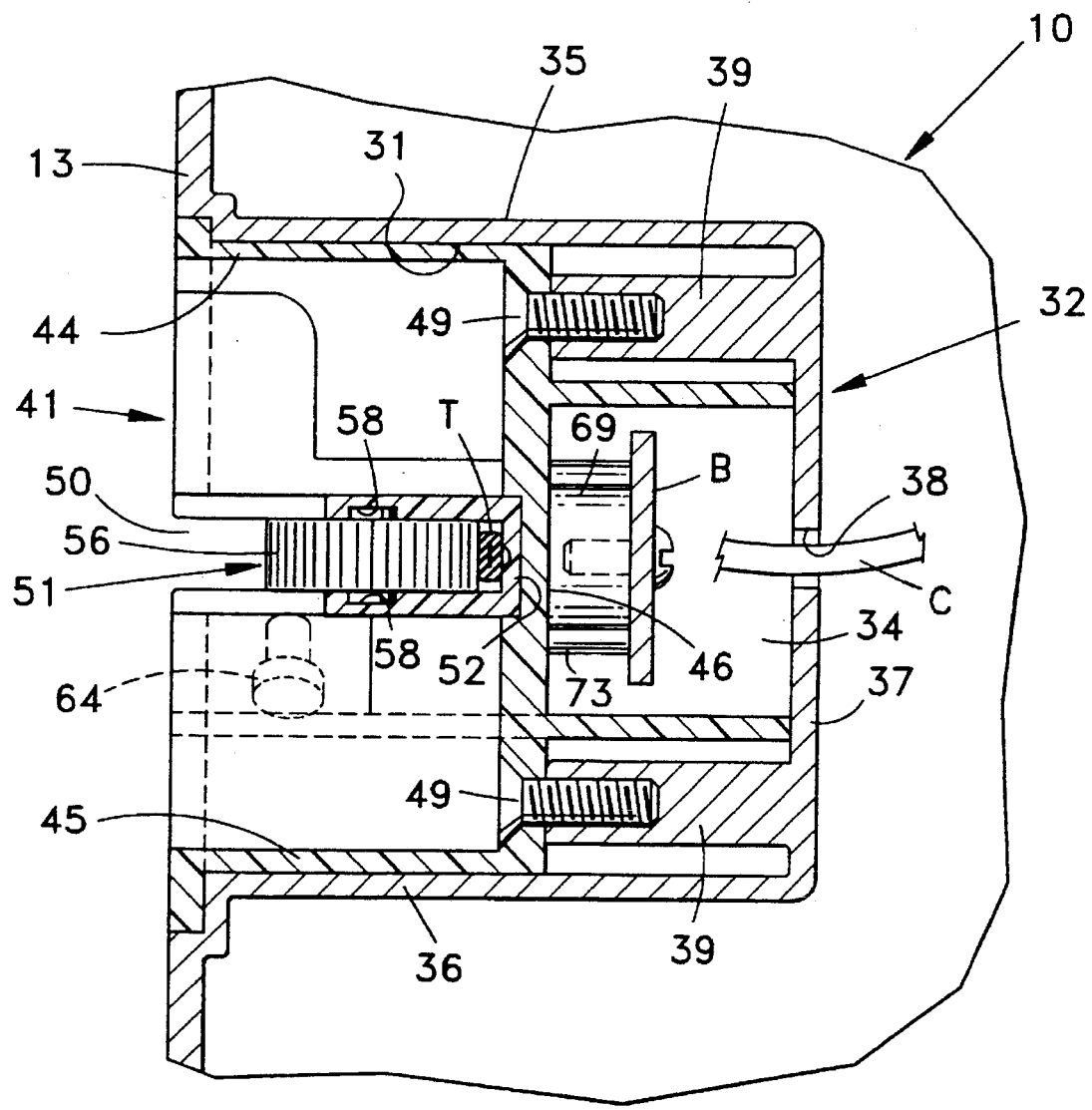
FIG. 3 is a fragmentary sectional view taken generally along the line 3—3 in FIG. 2 looking in the direction of the arrows.

Above the lever 16 the Front wall 13 has therein a large opening 31, which forms the forward, open end of a similarly shaped housing denoted generally by the numeral 32 in FIGS. 2 and 3. Housing 32 comprises spaced, parallel upper and lower walls 33 and 34 (FIG. 2), and spaced side walls 35 and 36 (FIG. 3) extending transversely of walls We and 34. Walls 33–36 are integral with and project rearwardly from the inside surface of the front wall 13 of housing 10, and are connected at their inner ends or edges by an integral, transverse end wall 37. Housing walls 33 and 34 have projecting inwardly from their forward edges elongate, registering slots 33' and 34' respectively, which register with the tubing channel 14 in the housing 10 to allow a section of the IV tube T to be inserted into the opening 31 in housing 10 as noted in greater detail hereinafter. End wall B7 has therethrough a small hole 38 through which extends a cable C for a purpose noted hereinafter.

Removably secured in the opening 31 in housing 32 is a roller clamp holder, which is denoted generally by the numeral 41 in FIGS. 1 to 3. Holder 41 has spaced, parallel, upper and lower walls 42 and 43 (FIG. 2), which are seated against the inside surfaces of the housing walls 33 and 34, respectively, and spaced side walls 44 and 45 that are seated against the inside surfaces of housing walls 35 and 36, respectively. Walls 42 and 43 have formed in their outer or forward edges tube accommodating slots 42' and 43', respectively, which register with the slots 33' and 34' in housing 32. Integral with and extending transversely between the walls 42–45 of the holder 41 is an end wall having a lower section 46 which extends parallel to and is spaced from the rear wall 37 of housing 32, and an inclined upper section 47 which extends, as shown in FIG. 2, diagonally upwardly and toward the rear housing wall 37 between section 46 and the upper wall 42 of the holder. Wall section 47 also forms a narrow notch section 48 immediately beneath the upper wall 42 of the holder adjacent the inner end thereof. Holder 41 is removably secured in housing 32 by two screws 49, which extend through section 46 of the holder end wall, and thread into the confronting ends of a pair of cylindrical bosses 39 that are integral with and project from rear wall 37 of housing 32.

Removably mounted in a rectangular opening 50 in the holder 41 is a conventional roller clamp, which is denoted generally by the numeral 51 in FIGS. 1 to 3. Clamp 51 has a hollow, generally rectangularly shaped lower end the inner wall 52 of which is seated as shown in FIG. 2 against the inside surface of section 46 of the end wall of holder 41, and has an upper, enlarged, generally hollow head section which has adjacent its inner end an inclined outer surface 53 that is seated against the inclined wall section 47 of holder 41. Also, the inner end of the clamp head section has formed thereon a narrow lip section 54, which seats in the recess 48 in the end wall of the holder 41.

Mounted for movement in vertical slot 55 (FIG. 1) in the front wall the roller clamp 51 is a disc-shaped roller 56. Roller 56 has projecting coaxially from opposite sides thereof reduced-diameter pins 57 which slide in opposed, registering, longitudinally extending grooves 58 that are formed in the confronting walls of the clamp. Grooves 58 are inclined slightly to the vertical, so that the lower ends thereof are positioned closer to the wall 52 of the clamp 51, while adjacent their upper ends the grooves 58 are inclined slightly as shown in FIG. 2 toward the front wall 13 of the housing 10. Consequently when the roller 56 is in its lowermost position as shown in full lines in FIGS. 1 to 3, its peripheral surface is forced by the grooves 58 inwardly against the adjacent tube T, thereby compressing the tube closed so that no fluid may flow from the supply thereof beyond the portion of the tube T which is crimped closed. Roller 56 has a knurled outer peripheral surface which enables an operator to shift the roller manually in a known manner between its full line position as shown in FIGS. 2 and 3, and its uppermost position, as shown by broken lines in FIGS. 1 and 2, where it engages and is stopped by a pair of lugs 59 (FIGS. 1 and 2) that project from the side walls of clamp 51. In its uppermost position the outer peripheral surface of roller 56 barely touches the tube T, so that the roller in no way impedes the flow of fluid through the tube.

For releasably securing the roller clamp 51 in the holder 41 an integral, flexible tab 40 projects downwardly (FIG. 2) from the upper wall 42 of holder 41 into the slot 55 in the roller clamp, and snugly and releasably into engagement with part of the top wall of clamp 51 adjacent the inner ends of the slots 33' and 42' that accommodate tube T. The tab 40 is shown merely by way of example, and could be replaced, if desired, by a metal tab, or the like, secured to holder 41 and projecting releasably into engagement with roller clamp 51.

As noted above, it is imperative that some means be provided for preventing accidental, undesirable opening of the roller clamp 51 at the time when the IV supply is connected by the tube T to the patient. As a precaution, therefore, the holder 51 is provided with sensor means in the form of a conventional photo detector or transistor having a light source or emitter 61 (Figs. 1 and 2) mounted in a recess in holder 41 to direct its beam transversely across the space 50 in which the roller clamp 51 is to be mounted, and a cooperating photo sensor element 62 mounted in a recess adjacent the opposite side of holder 41 to have its receptor lens positioned in registry with the beam emitted by emitter 61. In this manner, whenever the roller 56 of the roller clamp 51 is located in its uppermost or tube-open position, the beam emitted by the emitter 61 will be blocked by the roller 56, whereby preventing its beam from being directed onto the sensor 62.

Moreover, mounted in a similar recess adjacent the lower end of holder 41 is a photo cell device in the form of an emitter 64, for example an infra-red (IR) emitter, and an IR sensor 65, which are mounted in such a manner that the beam emitted by the emitter 64 strikes the surface of the roller 56, when the roller wheel 56 is in its lowermost position, thereby causing the beam to be reflected off of the surface of the roller 56 and onto the sensor 65. The advantage of this mechanism is that by using a reflected IR beam it prevents any accidental interruption of the beam from the emitter 64 to the sensor 65 as might occur if they were disposed coaxailly on opposite sides of the roller 56, in which case the insertion of any foreign object into the space between the emitter and sensor might accidentally interrupt the beam therebetween. By relying on the reflection of the beam from the emitter 64 to the sensor 65, the beam will arrive at the sensor only when the roller 56 itself is in the lowermost or clamping position. As noted hereinafter, this reflective sensing technique ensures that the roller clamp (and IV set) can only be removed from the electronic infusion device when the roller is in its lowermost (closed) position, thus preventing any free or uncontrolled flow of IV fluids to the patient.

An additional fail-safe device is represented by the solenoid 22, the armature 21 of which normally prevents undesirable opening of the lever 16, which in turn prevents the insertion of a tube into the housing 10, or the removal therefrom, until such time that the lever 16 has been swung from its closed to its opened or broken line position as shown in FIG. 3. The only logical occurrance that allows the lever 16 to be opened and thus the IV set to be inserted or removed, is again when the lower reflective type sensor device (64, 65) senses that the roller wheel 56 of the roller clamp is present in the closed position.

A printed circuit board B (FIGS. 2 and 3) is secured by a screw 67 to an internally threaded sleeve 68 that is secured coaxially in a boss 69 that projects from the rear surface of section 46 of the end wall of holder 41. Board B has thereon a connector (FIG. 2) which is connected by cable C to a power supply unit (not illustrated). Projecting from board B adjacent its lower end (FIG. 2) through a bore in another boss 73 that projects from wall section 46, and projecting through section 46 and into engagement with wall 52 of the roller clamp 51, is a normally open silicone rubber switch 74, which functions to detect the presence of roller clamp 51 in the holder 41. Switch 74 has a molded-in gasket to prevent fluid intrusion to board B, and has molded into the bottom thereof a conductive carbon pill which, when the switch is compressed, closes a circuit that energizes the photo detectors 61,62 and 64,65 as noted hereinafter.

As an additional precaution against the occurrence of accidental free flow when IV tubing is mounted in the device, lever 16 also operates special pressure plate which is designed to cooperate with the tube engaging fingers of the peristaltic pump unit, which is mounted in housing 10 beneath the roller clamp holder 41. Referring again to FIG. 1, and also to FIG. 6, numerals 81 denote a series of reciprocable fingers which form part of the pump unit, and which are positioned at one side of the registering section of channel 14 and IV tube T for operation in a conventional manner such as disclosed for example in U.S. Pat. No. 4,893,991. As disclosed in that patent, when the pump unit is operating, the fingers 81 are designed repeatedly and progressively to compress the confronting section of the IV tube T against a backup plate, or pressure plate, which is mounted in the pump housing opposite the fingers, and which in the present embodiment is denoted by numeral 83.

In the above-noted U.S. Pat. No. 4,893,991 the backup or pressure plate was mounted on a door hinged to the pump housing, so that when the door was closed the backup plate was swung into an operative position at one side of an IV tube. In the present embodiment however, pressure plate 83 is resiliently mounted by compression springs 82 for limited movement on an elongate spring housing 84, which is mounted to reciprocate beneath wall 11 and between opposite sides of the pump unit toward and away from the tubing channel 14. Secured at opposite ends thereof to the rear or left hand surface of housing 84, as shown in FIG. 1, is a rigid strap or bracket 85 which overlies one side of an elongate arcuate groove 86 formed in the rear surface of housing 84. The groove 86 registers with a pair of vertically spaced cams 87 that are secured to shaft 18 for rotation thereby.

Figure 4:
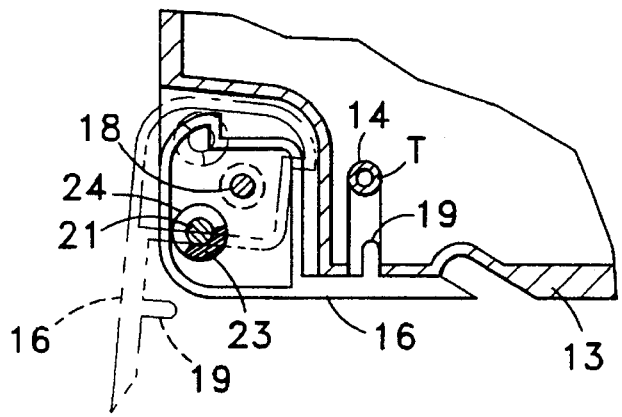
FIG. 4 is a fragmentary sectional view taken generally along the line 4—4 in FIG. 1 looking in the direction of the arrows.
Figure 6:
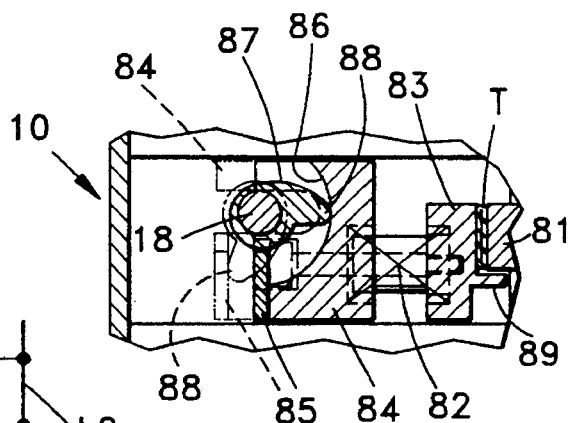
FIG. 6 is an enlarged fragmentary sectional view taken generally along the line 6—6 in FIG. 1 looking in the direction of the arrows.

When lever 16 is in its closed, locked position as shown in FIGS. 1 and 4, the curved outer ends 88 of cams 87 engage the back of housing 84 at the bottom of groove 86 and hold housing 84 and its pressure plate 83 in an advanced or operative position as shown by solid lines in FIGS. 1 and 6. In this position a narrow, longitudinally extending lip 89, which projects from the forward or right hand face of the pressure plate 83 as shown in the drawings, overlies and closes the outer end of that portion of tube channel 14 that extends through the pump unit. The lip 89 also positions tube T in proper registry with fingers 81, and pinches and occludes part of any improperly loaded tube to prevent free flow therethrough. Also at such time, at least one of the numerous fingers 81 will have urged a section of tube T with such force against the face of the spring loaded pressure plate 83 that the tube will be completely occluded in at least one spot, as shown for example in FIG. 6.

When lever 16 is swung to its open position (broken lines in FIG. 4), the cams 87 will be swung (clockwise in FIG. 6) approximately 90° by shaft 18 about the axis thereof, and in so doing the outer ends 88 of the cams will swing into engagement with the inside surface (right side in FIG. 1) of the strap 85, thus causing this strap and the attached housing 84 and plate 83 to be drawn slightly away from channel 14, and into their retracted, broken line positions shown in FIGS. 1 and 6. This causes the lip 89 on plate 83 to be retracted to a position in which it uncovers the registering section of channel 14 to permit withdrawal of tube T from the pump and channel 14.

Figure 5:
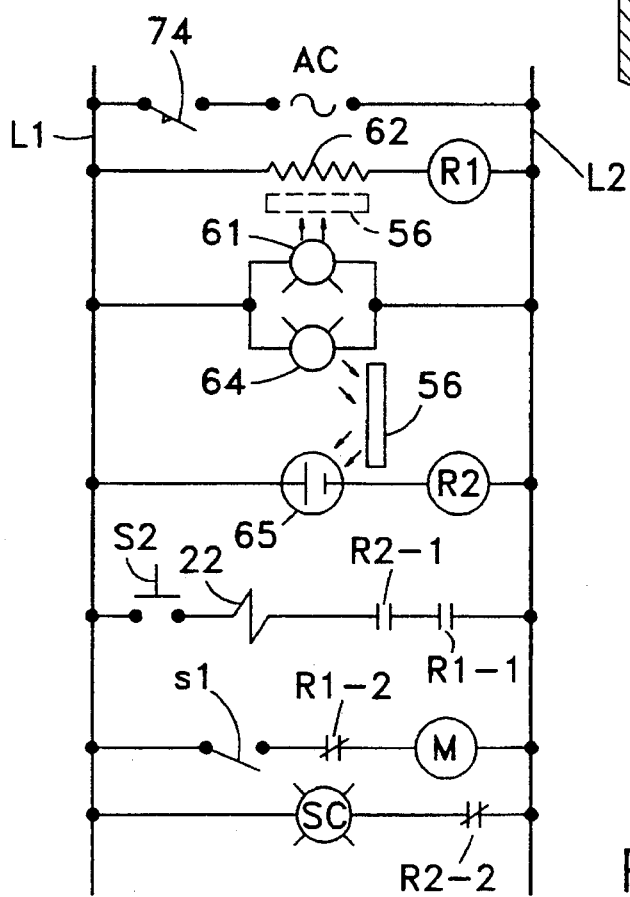
FIG. 5 is a wiring diagram showing one manner in which the electrical control means of the device may be wired to prevent accidental free flow of IV fluids to a patient.

Referring now to FIG. 5, L1 and L2 represent part of a control circuit across which an AC power supply, for example 115 volts, is adapted to be connected upon the closing of the switch 74, when clamp 51 is inserted in holder 41. Connected in parallel to each other between the lines L1 and L2 are the two emitters 61 and 64, which become energized upon the closing of switch 74. The receptor or light detector 62, which is disposed in coaxial registry with the emitter 61, is connected in series between lines L1 and L2 with a relay R1. The receptor 65, which receives light (for example IR light) from the emitter 64 only when the roller 56 is in its lowermost or tube-closing position, is connected in series with a second relay R2 between lines L1 and L2. The solenoid 22, which operates the lever-locking armature 21, is connected in series between the lines L1 and L2 with the LOAD/UNLOAD switch S2, together with the normally-open switch contacts R2-1 that are controlled by relay R2, and with the normally-open switch contacts R1-1 that are controlled by the relay R1. The motor M for operating the pumping section of the infusion device 10 is connected in series between lines L1 and L2 with normally-closed relay switch R1-2, and with a motor RUN-STOP switch S1, which as shown in FIG. 1 is one of a number of push-button switches located on the face of the housing of the device 10, along with number of other buttons which will not be described in greater detail herein, except for the button which is denoted in FIG. 1 as S2, the function of which is noted above. Connected in series between the lines L1 and L2 with a pair of normally closed switch contacts R2-2, also controlled by relay R2, is a warning lamp SC which, when energized, illuminates on the face of the housing of device 10 a warning message to "SHUT CLAMP".

In use, and assuming that switch 74 is closed and device 10 has already been loaded with an IV set the clamp 51 of which is fully seated in the holder 41, the emitters 61 and 64 will be energized, and the lever 16 will be secured in its closed position by the armature 21 of the solenoid 22. To remove the IV set and its associated roller clamp, and assuming switch S1 has been operated to turn off the pump motor M, it is absolutely necessary that the roller 56 be shifted downwardly into its lowermost or tube closing position so that light from the emitter 64 will energize the receptor 65, thus completing a circuit through the normally non-conducting receptor 65, and thereby energizing relays R1 and R2. Until relay R2 is energized, the solenoid 22 cannot be energized because the contacts R2–1 will be open. At the time that the roller 56 is in its lowermost position it does not interfere with the transmission of light from the emitter 61 to the receptor 62, so that at such a time relay R1 is energized, and its relay contacts R1–1 are therefore closed, and contacts R1–2 are open to prevent operation of motor M. Therefore as soon as the receptor 65 conducts, the relay contacts R2-1 also close. This enables the solenoid 72 to be energized upon the closing of the switch S2, which, if desired, can be a delayed-opening switch, which will give an operator ample time within which to swing the lever 16 from its closed to its opened position after operation of switch S2. As the lever 6 is opened, cams 87 retract pressure plate 83 away from tube T, and at the same time the lip 89 on the plate uncovers the section of tube T formerly gripped between plate 83 and the fingers 81. The IV set can then be removed from device 10.

In order to load the IV set into device 10 and assuming that lever 16 is closed the roller clamp 50 must be inserted into the holder 41 to its fully seated position, at which time it will close the switch 74, and will thus energize sensors 61, 62 and 64, 65. At such time, if the roller 56 is not in its lowermost or closed position, then relay R2 will be denergized, and its contacts R2–2 will be in their normally-closed position, thereby energizing the warning lamp SC to instruct the operator to shift the roller 56 downwardly to its tube-closing position. After the roller 56 has reached its lowermost position the switch S2 may be operated, as noted above to energize the coil of solenoid 22, thereby permitting the opening of the lever 16 and the insertion of tube T into the now-open section of channel 14 that extends through the pump unit. As noted above, when it is thereafter desired to close the lever 16, the camming surface 23 will enable the lever 16 to cam the spring-loaded armature 21 out of the way until the lever is fully closed, at which time the armature 21 will drop into the locking recess 23, and the lip 89 on plate 83 will have been shifted into its tube blocking position as shown in FIGS. 1 and 6. Also at such time at least one of the pump fingers 81 will have engaged and occluded the tube until such time that the pump is started.

From the foregoing it will be apparent that the present invention provides an improved electronic infusion device, which precludes the loading and unloading of an IV set and its associated roller clamp into and out of the device until such time that the roller 56 has been shifted to its tube-closing position. In this way undesirable accidental free-flow of an IV liquid is precluded from being delivered accidentally to a patient. Moreover, by utilizing the removable, modular holder 41, it is possible to make slight changes in the design of the holder to accommodate different types of roller clamps. In each case, however, the holder 41 will include the position sensing and safety device in the form of the two photoelectric devices which sense the position of the roller 50, and, in turn control satisfactory operation of the infusion device. More specifically, because the novel infusion device disclosed herein will use most standard gravity IV sets, which is a major cost advantage to most hospitals, no special components will be needed on the IV set. The roller clamp, standard on almost all IV sets, will be the "special" component on the IV set that will enable the user to utilize standard sets as "protected" sets for the first time only on the above-described device. By locking the IV set into the pumping zone until the roller clamp is completely closed, it is assured that there can be no instance of free flow for there is no possibility of an operator removing the IV set from the pump without following the proper steps. Furthermore, because there is only one set of steps to remove the IV set (i.e., prevent free flow there can be only one possible way one can obtain gravity flow rather than pump infusion via the associated IV set. These steps are outlined below:

(1) Press the run-stop key S1, (2) close the roller clamp wheel 56, (3) press the load/unload Key S2, (4) open the lever 16 to open pump channel, and (5) remove the IV set from tube channel. Thereafter, the operator may slowly roll the wheel 56 of the clamp toward the open position to initiate gravity flow while watching the drip chamber beneath supply bag for establishing proper drops per minute (i.e., flow rate).

Moreover, although the above-noted ECRI recommendations to hospitals on the issue of free-flow need not be followed or obeyed by all hospitals, these recommendations are usually held in high regard and looked upon as a "quasi industry" standard by most hospitals. ECRI believes that hospitals should start phasing out EID's that do not use anti free-flow infusion sets when a user fails to close the IV set's manual clamp. It is believed that the novel design disclosed herein meets such "quasi standard", because the manually operated roller clamp must be completely closed before being removed from the pump, the set is protected against free-flow until this and only this situation occurs. The module that allows this to occur is the roller clamp holder and the associated sensing technique,as well as, the method with which the tubing is locked into the pump so that the tube is continuously blocked off at all times except during the normal infusion period. Also, switch R1–2 prevents operation of the pump motor M until such time that the roller clamp wheel 56 is in its open, non-occluding position.

While the circuit of FIG. 5 has been described in connection with certain electrical elements, it will be apparent to one skilled in the art, that equivalent electronic or solid state elements could be utilized without departing from this invention. Moreover, although this invention has been illustrated and described in connection with only certain embodiments thereof, it will be apparent that it is capable of still further B modification, and that this application is intended to cover any such modification as may fall within the scope of one skilled in the art, or the appended claims.

We claim:

1. A device for infusing IV fluids into a patient through an IV set of the type including an IV tube and associated clamp having mounted thereon a manually operable crimping element movable on the clamp selectively between an open positioning which it permits the flow of fluid through the tube and a closed position in which it compresses the tube and blocks the flow of fluid therethrough, comprising a housing having therein an IV tube channel and a mechanism for infusing fluid through an IV tube seated in said channel and operatively connected to said mechanism, a clamp holder removably secured in said housing, and having therein a recess opening on the exterior of said housing, and configured removably to support therein the clamp of an IV set with the IV tube thereof seated in said channel and operatively connected to said infusing mechanism, and with said crimping element facing outwardly of said opening to permit manual operation thereof, first seeing means on said holder for detecting the presence of said clamp when the latter is supported in said holder, second sensing means on said holder operative, when said clamp is supported in said recess, to detect when said crimping element of the clamp is in its closed position, and safety means on said housing controlled by said sensing means and operable to enable said IV tube to be disconnected from said mechanism only when said crimping element is in its closed position.

2. A device as defined in claim 1, wherein said second sensing means comprises an electrical circuit, including a light sensitive detector mounted in said holder and confronting on said recess adjacent one end thereof, and an emitter mounted in said holder adjacent said detector and operative, when said crimping element of the clamp is in its closed position, to direct a beam of light onto said element for reflection thereby onto said detector, said detector being operative to enable operation of said safety means upon sensing said light reflected from said crimping element.

3. A device as defined in claim 2, wherein said emitted light and reflected light are in the infrared region of the spectrum.

4. A device as defined in claim 2, wherein said circuit further includes a second light sensitive detector mounted in said holder adjacent the opposite end of said recess and positioned o confront said crimping element when said element is in its open position, and a second emitter mounted in said holder adjacent said second detector to direct a beam of light onto said second detector, when said crimping element is not in its open position, and to have the last-named beam of light blocked off by said element from said second detector, when said element is in its open position.

5. A device as defined in claim 1, including resilient detent means on said holder-engagable with a recess in said clamp upon insertion thereof Into said holder, thereby removeably to secure said clamp in said holder.

6. A device as defined in claim 1, wherein said safety means comprises channel blocking means mounted on said housing for movement manually between an open position in which said blocking means enables insertion of said IV tube into an operative position in which it is seated in said channel and operatively connected to said infusing mechanism, and a closed position in which said blocking means prevents removal of said tube from its operative position, and locking means preventing movement of said channel blocking means to its open position when said crimping element of said clamp is not in its closed position.

7. A device as defined in claim 6, wherein said locking means comprises a solenoid-operated plunger mounted on said housing for movement into and out of a locking position in which it releasably secures said channel blocking means in its closed position when said crimping element is not in its closed position.

8. A device as defined in claim 7, wherein said channel blocking means comprises a lever pivotally mounted adjacent one end thereof on said housing for swinging movement manually into a closed position in which the opposite end thereof overlies part of said IV tube channel to prevent an IV tube from being inserted into or removed from an operative position with respect to said infusing mechanism, and an open position in which said opposite end thereof is swung away from said channel to-uncover said part thereof, and said solenoid-operated plunger has one end thereof seated a recess in said lever to prevent swinging movement thereof, when said lever is in its closed position and said crimping element is not in its closed position.

9. A device as defined in claim 6, wherein said infusing mechanism comprises a peristaltic pump unit having a section of said tube channel extending therethrough, and disposed to have seated n said section a registering portion of an IV tube to pump fluid therethrough upon operation of said pump unit, a pressure plate as mounted in said pump unit adjacent one side of said channel section for manual movement toward the opposite side of said channel section to an advanced position in which it operatively connects said registering portion of said tube to said pump unit, and for manual movement away from said opposite side of said channel section to a retracted position to disconnect said registering portion of said tube from said pump unit, and said channel blocking means comprises a lip projecting from said pressure plate for movement thereby to a closed position in which said lip overlies and covers said channel section when said plate is in its advanced position, and to an open position in which said lip uncovers said channel section when said plate is moved to its retracted position.

10. A device as defined in claim 9, wherein upon being moved to its advanced position said pressure plate is operative to occlude the flow of fluid through said registering portion of said tube except when said pump unit is operating.

11. A device as defined in claim 1, wherein said holder includes an end wall extending transversely across and closing the bottom of said recess, and said end wall is removably secured to said housing by fastening means which are accessible through said recess from the exterior of said housing.

12. A device as defined in claim 11, wherein said sensing means and said safety means are electrically operable, electric circuit means are mounted on said holder for controlling the operation of said sensing means and said safety means, said circuit means includes a switch having an operating arm extending into said recess for engagement and operation by said clamp, when said clamp is mounted in said recess, and said switch is operative upon engagement of its operating arm by said clamp to operate said sensing means and said safety means.

13. A device as defined in claim 12, wherein said circuit means further includes alarm means controlled by said switch and said sensing means, and operative to be energized upon operation of said switch by said clamp, when said crimping element is not in its closed position.

14. In a fluid infusion device of the type having a housing containing a mechanism for infusing fluid through an IV tube operatively connected to said mechanism, the improvement comprising, an IV tube clamp holder having a clamp holding recess in one end thereof, means releasably securing said holder in said housing with said clamp holding recess opening on the exterior of said housing, means in said holder for releasably supporting in said recess an IV set, said set comprising an IV tube clamp having thereon a tube clamping element movable between the opening and tube closing positions with respect to a portion of an IV the that extends through said clamp for connection to said mechanism, first sensing means on said holder for detecting when said clamping element is in its tube closing position, and second sensing means on said holder for detecting when said clamping element is in its tube opening position.

15. In a fluid infusion device as defined in claim 14, wherein said first sensing means comprises an emitter mounted on said holder adjacent one side of said recess and operative to direct a beam of light onto said clamping element when said element is in said tube closing position, and a light sensitive detector mounted in said holder to receive light from said emitter only when said element is in its tube closing position.

16. In a fluid infusion device as defined in claim 15, wherein said light sensitive detector is mounted in said holder adjacent said one side of said recess to confront said clamping element, when said element is in its tube closing position, thereby to receive light from said emitter by reflection from said element.

17. In a fluid infusion device as defined in claim 14, wherein said means releasably supporting said IV set in Said recess includes resilient detent means interposed between said holder and said clamp frictionally to retain said clamp releasably in said recess.

18. An infusion device for infusing IV fluids into a patient through an IV set of the type including an IV tube and associated clamp having a crimping element movable thereon selectively to a closed position in which it blocks the flow of fluid through said tube, comprising a housing having therein an IV tube channel and a peristaltic pump unit having a section of said tube channel extending therethrough, a clamp holder removably secured in said housing, and having therein a recess configured removably to support therein the clamp of an IV set with the IV tube thereof seated in said channel and with a portion of the IV tube disposed in operative registry with said pump nit, a pressure plate mounted in said pump unit adjacent one side of said channel section for movement toward the opposite side of said channel section to an advanced position in which it operatively connects said registering portion of said tube to said pump unit, and for movement away from said opposite side of said channel section to a retracted position to disconnect said registering portion of said tube from said pump unit, channel blocking means mounted on said pressure plate for movement thereby to a closed position in which said blocking means overlies and covers said channel section when said plate is in its advanced position, and to an open position in which said blocking means uncovers said channel section when said plate is moved to its retracted position, electronic sensing means on said holder operative, when said clamp is supported in said recess to detect when said crimping element of the clamp is in its closed position, and safety means on said housing operative to enable said pressure plate to be moved to its retracted position only when said crimping element is detected by said sensing means to be in its closed position.

19. An infusion devices defined in claim 18, wherein said safety means comprises locking means releasably securing said pressure plate in its advanced position, and switch means mounted on said housing and operable only when said crimping element is in its closed position to effect release of said locking means, thereby to allow movement of said pressure plate to its retracted position.

20. An infusition device as defined in claim 19, wherein said locking means comprises a solenoid-operated plunger mounted on said housing for movement into and out of a locking position in which it releasably secures said pressure plate in its advanced position when said crimping element is not in its closed position, and said switch means includes a manually-operable switch mounted on said housing and operable to move said plunger out of its locking position only when said crimping element is in its closed position.

* * * * *